United States Patent
Wiesemann

(10) Patent No.: US 8,727,770 B1
(45) Date of Patent: May 20, 2014

(54) DENTAL APPLIANCE

(76) Inventor: Ryan B. Wiesemann, Bowling Green, KY (US)

( * ) Notice: Subject to any disclaimer, the term of this patent is extended or adjusted under 35 U.S.C. 154(b) by 843 days.

(21) Appl. No.: 12/713,900

(22) Filed: Feb. 26, 2010

(51) Int. Cl.
*A61C 3/00* (2006.01)

(52) U.S. Cl.
USPC .......................................................... 433/19

(58) Field of Classification Search
USPC ........................................ 433/19, 2, 18, 8, 24
See application file for complete search history.

(56) References Cited

U.S. PATENT DOCUMENTS

| | | | |
|---|---|---|---|
| 3,683,502 A * | 8/1972 | Wallshein | 433/21 |
| 4,671,766 A | 6/1987 | Norton | |
| 5,443,384 A * | 8/1995 | Franseen et al. | 433/18 |
| 5,683,244 A | 11/1997 | Truax | |
| 5,848,891 A * | 12/1998 | Eckhart et al. | 433/19 |
| 5,871,350 A | 2/1999 | Clark et al. | |
| 5,957,686 A * | 9/1999 | Anthony | 433/19 |
| 6,099,304 A | 8/2000 | Carter | |
| 6,364,659 B1 * | 4/2002 | Lotte | 433/8 |
| 6,368,106 B1 * | 4/2002 | Clark | 433/19 |
| 6,394,799 B1 * | 5/2002 | Testa et al. | 433/19 |
| 6,726,473 B1 * | 4/2004 | Guray | 433/6 |
| 6,884,067 B2 * | 4/2005 | Tuneberg | 433/19 |
| 6,913,460 B2 | 7/2005 | Cleary et al. | |
| 6,932,598 B1 | 8/2005 | Anderson | |
| 7,018,203 B2 | 3/2006 | Clark | |
| 7,174,895 B2 | 2/2007 | Thornton et al. | |
| 2008/0102414 A1 * | 5/2008 | Abels et al. | 433/19 |

OTHER PUBLICATIONS

Nina Heinig, DDS, Why the Forsus Fatigue Resistant Device is My Treatment of Choice, Orthodontic Perspectives, 2007, pp. 18-20, vol. XIV No. 1, 3M Unitek, Monrovia, CA, USA.

* cited by examiner

*Primary Examiner* — Ralph Lewis
(74) *Attorney, Agent, or Firm* — Middleton Reutlinger; James E. Cole

(57) ABSTRACT

The dental appliance is a generally L-shaped, with a vertical section and a horizontal section. The horizontal section extends from the main body section of the vertical section. The horizontal section has a smooth and continuous upper surface and lower surface which extends from a first end to a second end. The horizontal section extends from the first end on the facial side of the teeth toward the second end on the lingual side of the teeth, stretching across the occlusal surfaces.

10 Claims, 8 Drawing Sheets

DENTAL APPLIANCE

A variety of methods are used by orthodontists to address a deep bite. One of the most used methods is for the orthodontist to bond pads to the lingual side of the patient's upper front teeth. The pads prevent the upper front teeth from making contact with the lower front brackets. These pads are placed with a chemical bond and undergo significant forces as the lower front teeth strike them, which makes them subject to frequent failure. Once the pads have failed, the lower front brackets are typically forced off by the upper front teeth as well.

Another common method used by orthodontist to address a deep bite is to apply large mounds of cement to a patient's lower molars. This has the effect of keeping the patient's bite open and prevents the lower front brackets from being forced off by the upper front teeth. The chemical bonding of the cement mound is subject to failure along with the fact that removing large mounds of cement from the lower molars leads to the risk of inadvertently losing tooth structure during the removal process.

A device in the prior art is described in U.S. Pat. No. 6,726,473 and was developed by Enis Yaser Guray. The device shown in this reference does not use chemical bonding to attach to the teeth but rather is applied to the molar band. The structure of the Guray device does not provide a solid and continuous surface upon which to actually raise the user's bite, which can cause uneven wear of the user's teeth. Additionally, in order to be secured to the patient's molar band, the Guray device must be attached to both the facial and lingual side of the band, making it difficult to install. Once the Guray device has been attached to the molar band, the ability to reuse it is questionable as the bending of the attachment sections may not be easily released and reattached to the molar band.

Due to the lack of good options available in the field, many orthodontist opt to delay placement of brackets on the lower front teeth until a patient's deep bite has been somewhat corrected by use of the upper brackets. This has the undesirable side effect of lengthening the patient's treatment period.

The present invention has been designed to fill the need of the orthodontic community. An orthodontist can easily insert the present invention onto devices which are already present in a patient's mouth. Additionally the present invention can be easily removed to check on the patient's progress and then just as easily reattached. The present invention serves to provide an effective and quick treatment option for the orthodontist to allow the patient's treatment of the lower teeth to progress, without the fear of the lower front brackets being forced off.

DETAILED DESCRIPTION OF THE DRAWINGS

Figure 1:
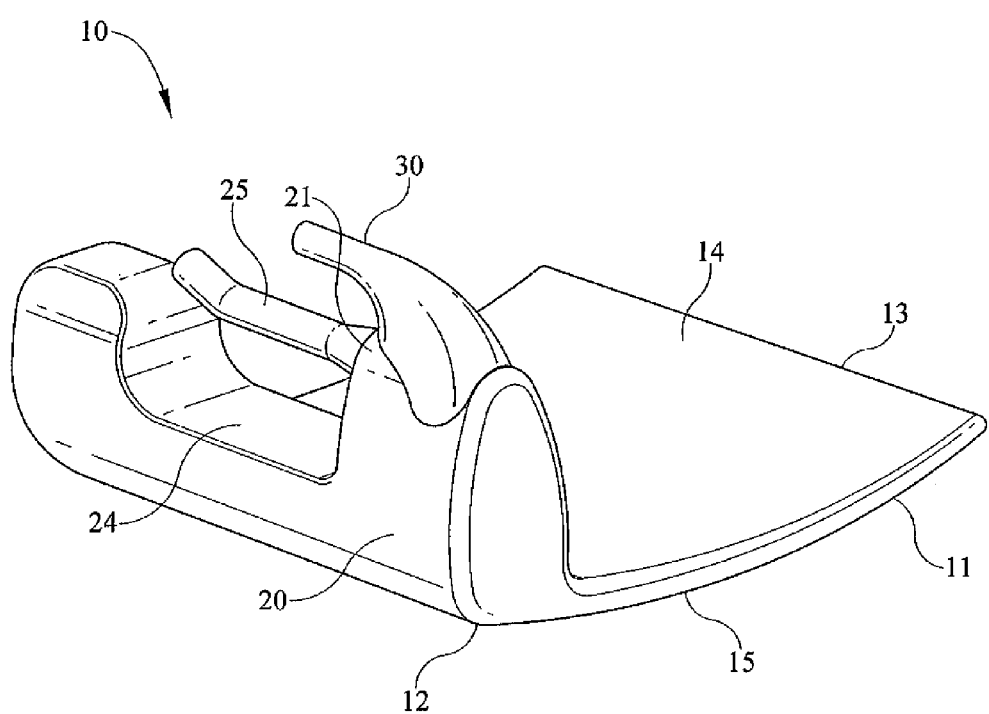
FIG. 1 is a perspective view of the present invention.
Figure 2:
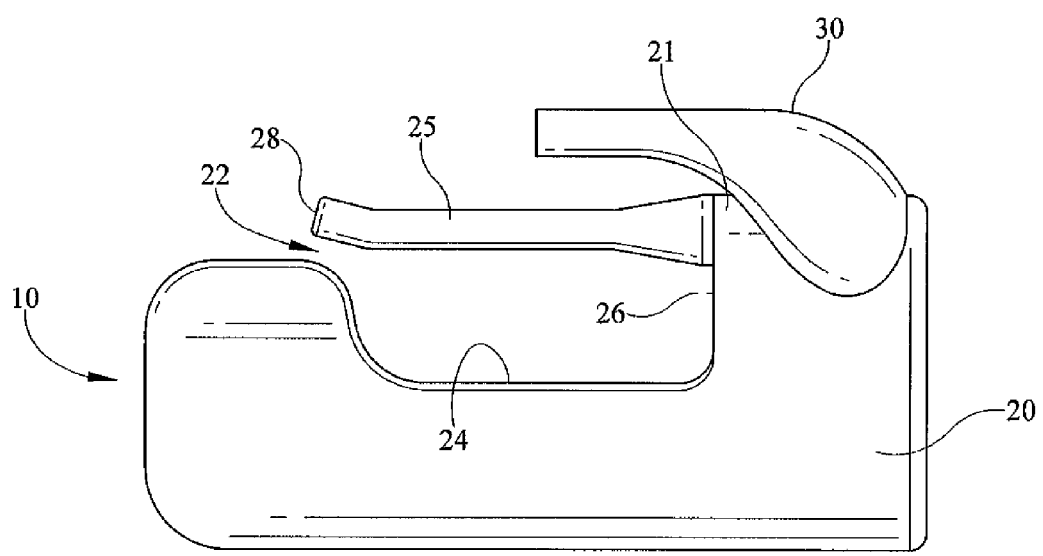
FIG. 2 is a side elevational view of the present invention.

The present invention 10 as is shown in FIGS. 1 and 2 is a substantially L-shaped, with a vertical section 20 and a horizontal section 11. The horizontal section 11 includes a smooth and continuous upper surface 14 and lower surface 15 which both extend from a first end 12 to a second end 13.

The vertical section 20 is melded with the first end 12 of the horizontal section 11 and extends upwardly making the present invention 10 substantially L-shape or a curved shape. At the upper end of the vertical section is a connection means which is used to connect to a variety of orthodontic appliances. In a preferred embodiment of the present invention 10 the vertical section 20 includes a recess 24 which is formed in its top edge 21. A laterally extending tongue 25 extends from the side wall 26 of the recess 24 substantially across the width of the recess 24. The tip of the tongue 28 is slightly upturned, so as to allow an opening 22 between the top edge 21 of the vertical section 20 and the tongue tip 28. This opening 22 allows the tongue 25 to act as a fastener for the present invention 10.

Figure 3:
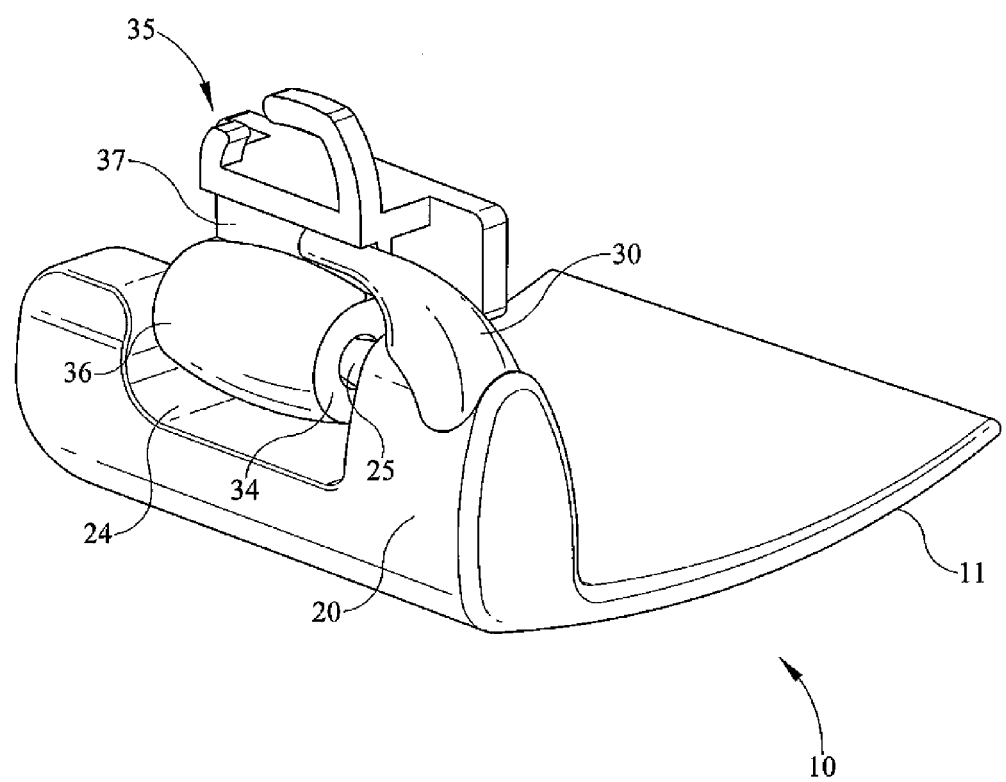
FIG. 3 is a perspective view of the present invention inserted within the head gear tube of a buccal tube.
Figure 4:
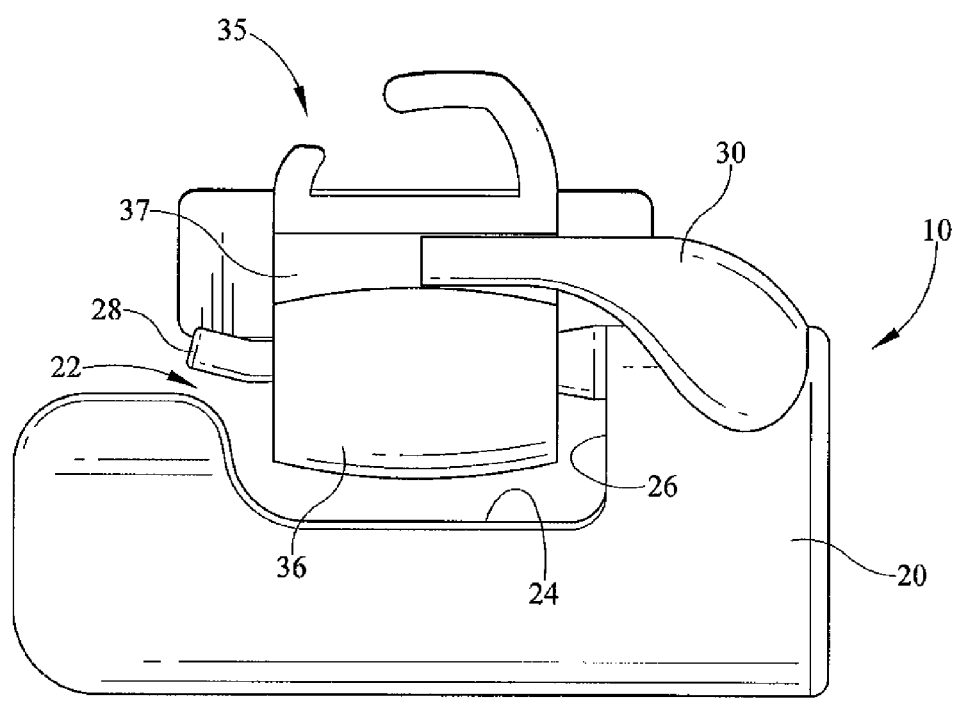
FIG. 4 is a side elevational view of the present invention inserted within the head gear tube of the buccal tube.

The present invention 10 can be used with a variety of frequently used orthodontic appliances. One such appliance is the head gear tube 36. A head gear tube 36 may be placed directly on an orthodontic bracket. The orthodontic bracket may be placed directly onto a molar band which is placed on a patient's first molars. Another way a head gear tube 36 may be utilized is though a buccal tube 35, which is shown in FIGS. 3 and 4. A buccal tube 35 connected to a first molar can by be utilized by an orthodontist for a variety of uses. Typical buccal tubes 35 also include fittings for other accessories such as a head gear tube 36.

In the situation where a patient has a buccal tube 35 with a head gear tube 36, the laterally extending tongue 25 of the present invention 10 may be inserted into the opening of the head gear tube 36. The outer rim 34 of the head gear tube 36 can slip over the tongue 25 and into the recess 24. The opening 22 created by the top edge 21 of the vertical section 20 and the tip of the tongue 28 allows for the outer rim 34 of the head gear tube 36 or similar device to be slid onto the tongue 25 and pushed into the recess 24. The tip of the tongue 28 may include a slight upward tilt which serves to assist in placement of the tongue 25 of the present invention 10 within the head gear tube 36. Once the head gear tube 36 or similar connection device is slid into the recess 24 it is held securely by the recess 24 and the tongue 25 structure so as to prevent the inadvertent removal of the present invention 10.

Once the present invention 10 is secured on to a patient's buccal tube, it can be removed if desired. By applying downward pressure to the tope edge 21 of the vertical section 20 the opening 22 between the tip of the tongue 28 and the top edge 21 of the vertical section 20 is enlarged, allowing the tongue 28 to be slid from the opening on the head gear tube 36. This feature allows the orthodontist to remove the present invention 10 and check a patient's progress, with the option to reinstall the same device back on to the patient's teeth.

The present invention may also include a laterally extending anti-rotation arm 30 which extends upward from the top edge 21 of the vertical section 20 and is substantially parallel to the laterally extending tongue 25. This anti-rotation arm 30 is designed to reside on the facial side of the teeth and is intended to prevent outward rotation of the present invention 10 when in use. When in use with a buccal tube 35, the anti-rotation arm 30 resides in the channel 37 located above the head gear tube 36, as is shown in FIGS. 3 and 4.

When the present invention is in use, the vertical section 20 resides on the facial side of the teeth and the horizontal section 11 extends toward the lingual side of the teeth across the occlusal surface of the teeth. When the upper and lower teeth come together, the horizontal section 11 prevents the full closure of the patient's mouth and provides for continuous and solid upper and lower surfaces, 14, 15 for both the upper and lower teeth to rest upon. The horizontal section 11 may vary in thickness, depending upon the needs of the patient. When the present invention is in use, it stops the upper front teeth from coming into contact with the brackets on the lower front teeth, thus allowing an orthodontist to initiate treatment on the lower teeth at the same time that treatment is initiated on the upper teeth. When treating deep bite, the orthodontist may place the dental appliance 10 on both sides of the top back teeth or on the lower back teeth instead.

Figure 5:
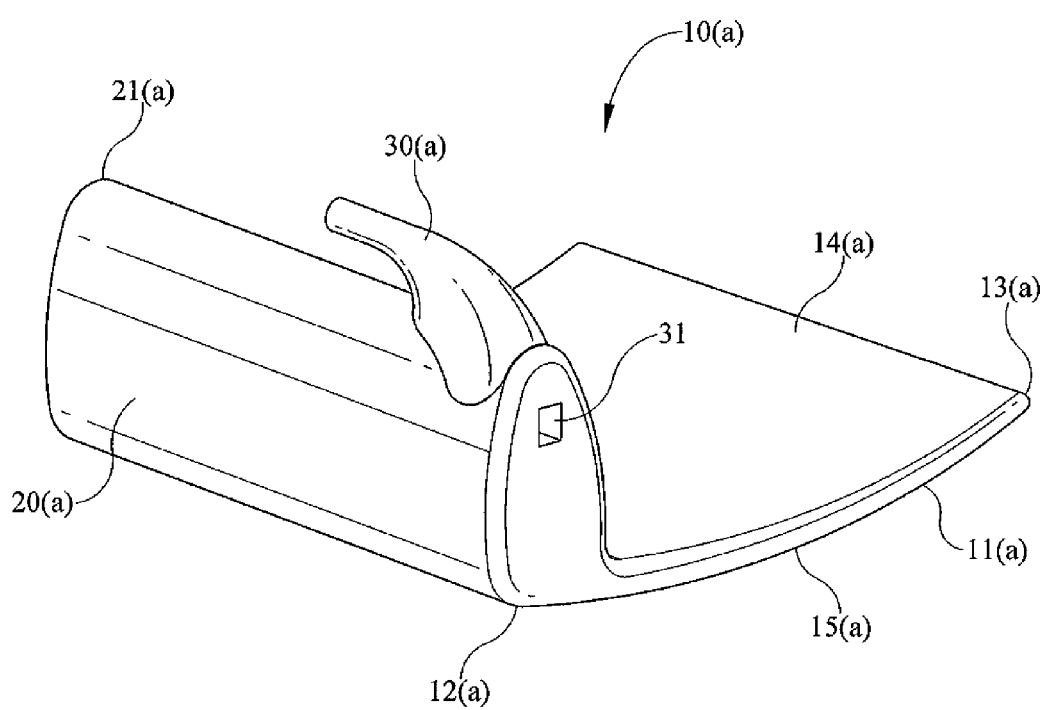
FIG. 5 is a perspective view of an alternative embodiment of the present invention.

An alternative embodiment of the present invention 10(a) with a different connection means to connect to an orthodontic appliance is shown in FIG. 5. This alternative embodiment of the present invention 10(a) includes a horizontal section 11(a) and a vertical section 20(a). The horizontal section 11(a) has a first end 12(a) and a second end 13(a). The first end 12(a) melds with the vertical section 20(a) and is substantially L-shaped or a curved shaped.

Extending laterally along the vertical section 20(a) is a channel 31. When the alternative embodiment of the present invention 10(a) is in use, the arch wire, which is used in connection with a patient's braces, is placed though the channel 31 and thus serves as a means to secure the alternative embodiment of the present invention 10(a) in the patient's mouth. Additionally, an anti-rotation arm 30(a) may extend from the top edge 21(a) of the vertical section 20(a) and further extends laterally and substantially parallel to the channel 31 for the arch wire.

Figure 6:
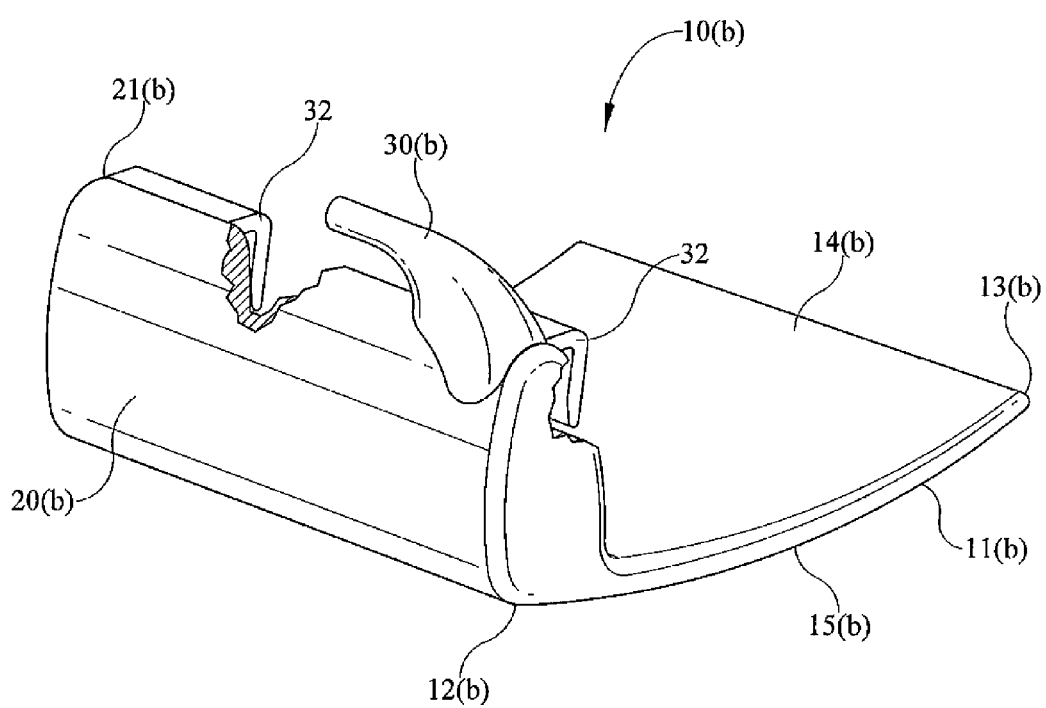
FIG. 6 is a perspective view of an alternative embodiment of the present invention.

Another embodiment of the present invention 10(b) with an alternative connection means is shown in FIG. 6. This embodiment also has a horizontal section 11(b) and vertical section 20(b). The horizontal section 11(b) has a first end 12(b) and a second end 13(b) which are connected by smooth continuous upper and lower surfaces 14(b), 15(b). The first end 12(b) melds with the vertical section 20(b) and is substantially L-shaped or a curved shaped.

The vertical section 20(b) melds with the first end 12(b) of the horizontal section 11(b) and is substantially L-shaped or a curved shaped. Extending inwardly from top edge 21(b) of the vertical section 20(b) is at least one clip structure 32 which is capable of being slipped over the arch wire, which is used by a patient with braces. The clip structure 32 extends away from the vertical section 20(b) on the side which the horizontal section 11(b) extends. The clip structure 32 serves as the means to secure the alternative embodiment of the present invention 10(b) to the patient's braces. An anti-rotation arm 30(b) may extend upward from the top edge 21(b) of the vertical section 20(b) and further extends laterally and substantially parallel to the top edge 21(b) of the vertical section 20(b).

With both of these alternative embodiments of the present invention 10(a) and 10(b), the use of a buccal tube 35 with accessories such as a head gear tube 36 would not be necessary to attach the device in a patient's orthodontic devices.

Figure 7:
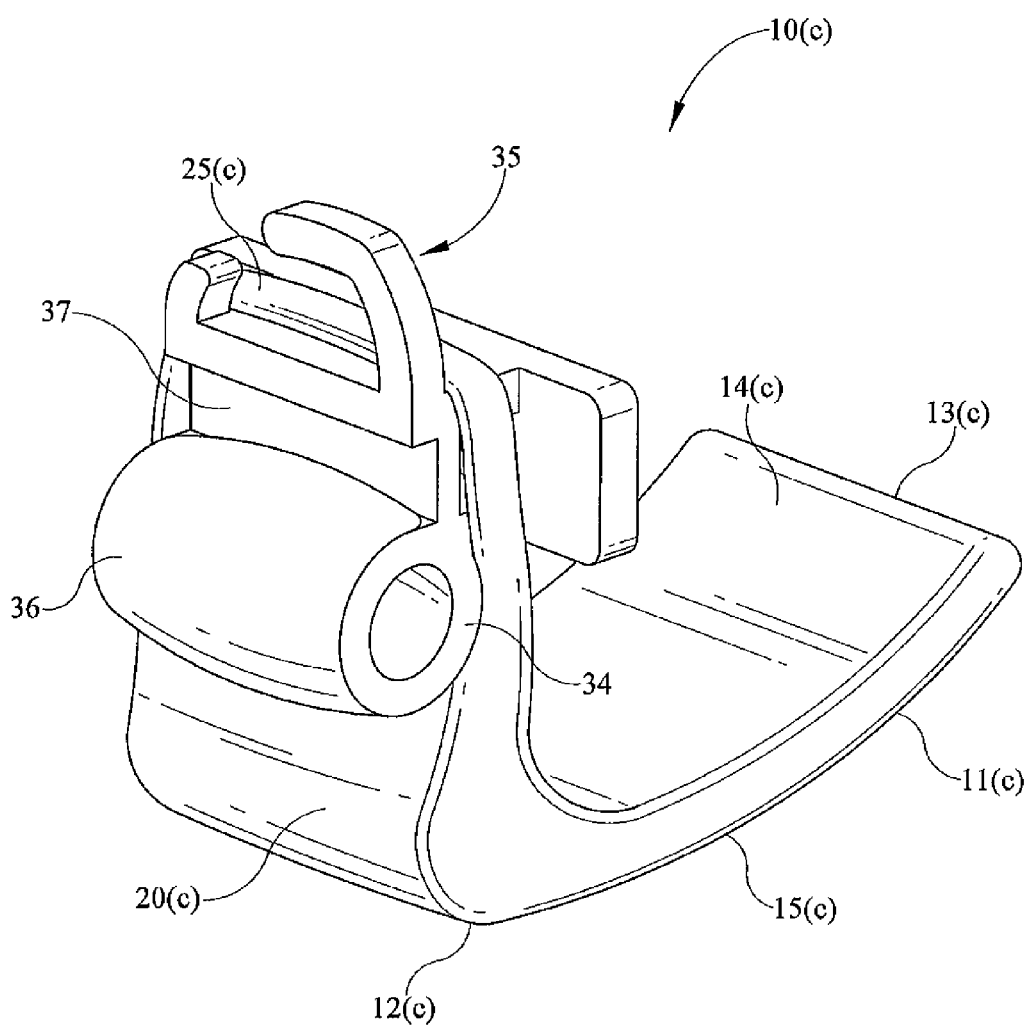
FIG. 7 is a perspective view of an alternative embodiment of the present invention.
Figure 8:
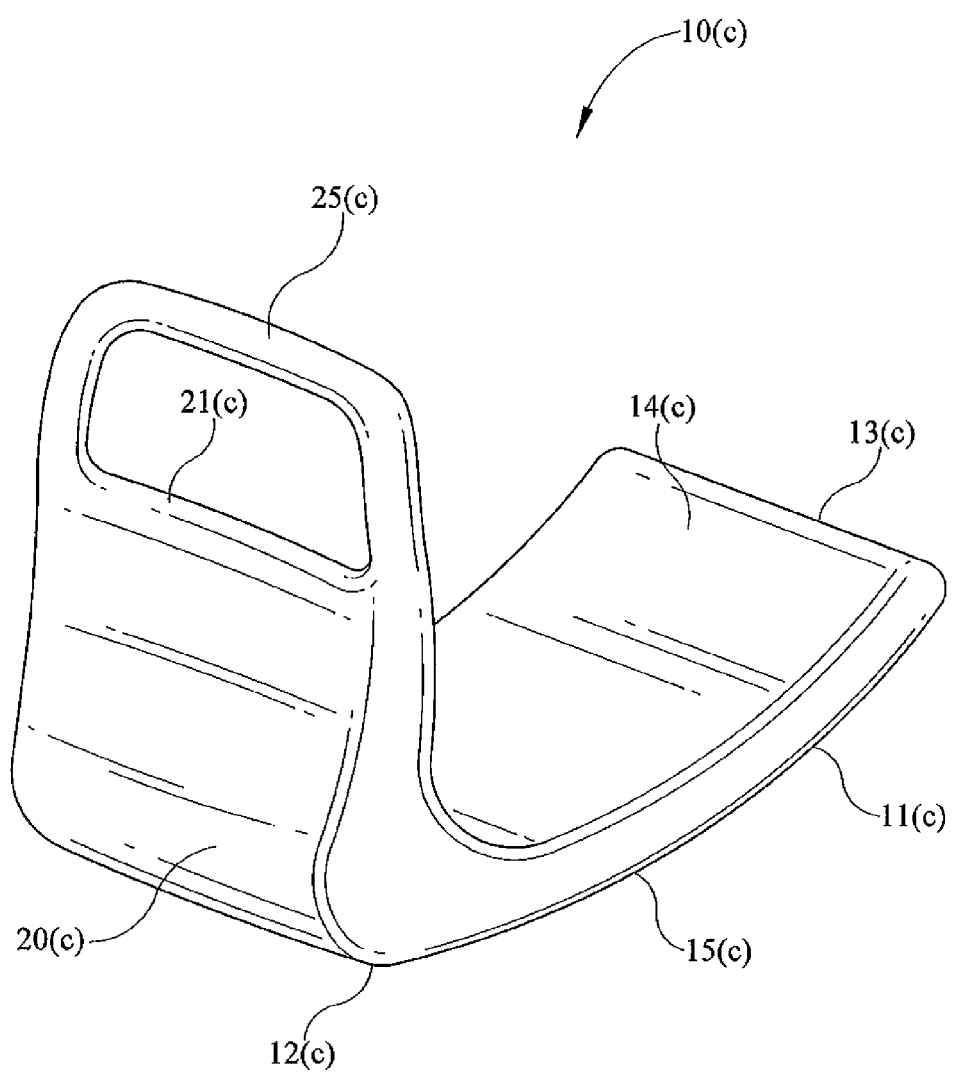
FIG. 8 is a perspective view of an alternative embodiment of the present invention.

The present invention may be made of a semi-rigid plastic or a firm elastic material. Embodiments made with the firm elastic material provide for additional stretch capacity. Shown in FIGS. 7 and 8 is an embodiment of the present invention 10(c) which has a alternative connection means. This embodiment of the present invention 10(c) may be made of firm elastic material. The embodiment 10(c) has a horizontal section 11(c) and vertical section 20(c). The horizontal section 11(c) has a first end 12(c) and a second end 13(c) which are connected by smooth continuous upper and lower surfaces 14(c), 15(c). The first end 12(c) melds with the vertical section 20(c) and is substantially L-shaped or a curved shaped.

This alternative embodiment 10(c) is placed in use in conjunction with an orthodontic bracket, head gear tube 36, a buccal tube 35 or a similar type of orthodontic device. FIG. 7 shows the alternative embodiment 10(c) is use with a buccal tube 35. The vertical section 20(c) includes a top edge 21(c) with a top handle 25(c) above. The handle 25(c) may be stretched and placed around an orthodontic device, such as a buccal tube 35 as the means of attachment. Once the handle 25(c) is in place, the alternative embodiment 10(c) is held securely in place.

Although the invention has been described in detail with reference to preferred embodiments and specific examples, variations and modification exist within the scope and spirit of the invention as described and defined in the following claims.

The invention claimed is:

1. A dental appliance, comprising;
   a substantially L-shaped elastic device with a vertical section and a horizontal section;
   said horizontal section having an upper surface and lower surface which may be disposed between engaging surfaces of a user's teeth;
   said vertical section includes a top edge;
   an arm extending upwardly and laterally from adjacent said top edge of said vertical section and spaced from said top edge; and,
   an opening between said top edge and said arm capable of receiving a orthodontic appliance therein.

2. The dental appliance of claim 1 wherein said horizontal section has a first end and a second end, with a continuous surface connecting said first and second ends.

3. The dental appliance of claim 1 wherein said vertical section includes a recess formed in the top edge of said vertical section, said recess including a side wall and said side wall including a tongue extending substantially across said recess.

4. The dental appliance of claim 1 wherein an opening extends laterally through said vertical section.

5. The dental appliance of claim 1 further comprising a clip structure extending from said top edge of said vertical section and above said horizontal section.

6. The dental appliance of claim 1 wherein said arm comprises a top handle extending above said top edge of said vertical section.

7. A dental appliance comprising;
   a substantially curved shaped device with a vertical section and a horizontal section;
   said horizontal section capable of being positioned to interface a user's upper and lower teeth, said horizontal section including a first end and a second end, with a continuous surface connecting said first and second ends with said first end melded with said vertical section;
   said vertical section capable of being disposed along a cheek-side outer face of a tooth including a top edge and an arm extending upwardly from and spaced above said upper edge;
   a space between said arm and said upper edge capable of receiving an orthodontic appliance.

8. The dental appliance device of claim 7 further comprising a recess formed in said vertical section, with said recess including a side wall and said side wall having a tongue extending substantially across said recess.

9. A method of using a dental appliance having a vertical section and a horizontal section, said vertical section having an opening capable of receipt of an orthodontic appliance, comprising the steps of:
   inserting said appliance in a user's mouth;
   engaging one of a lower surface of an upper tooth or a upper surface of a lower tooth with said horizontal section;
   positioning said vertical section along a cheek-side outer surface of said one of a upper tooth or a lower tooth;
   slipping said orthodontic appliance into said opening of said vertical section.

10. A dental appliance, comprising:
   a substantially L-shaped elastic device having a vertical section and a horizontal section;
   said horizontal section having an upper surface and a lower surface which may be disposed on one of an upper surface of a lower tooth or a lower surface of an upper tooth;
   said vertical section capable of being disposed along a cheek-side outer face of one of said lower tooth and said upper tooth, said vertical section including a top edge and further including a handle defining a space wherein an orthodontic appliance is capable of being received.

* * * * *